United States Patent
Hörth et al.

(10) Patent No.: US 6,846,300 B2
(45) Date of Patent: Jan. 25, 2005

(54) MULTI-COMPONENT MIXING CAPSULE, IN PARTICULAR FOR DENTAL PURPOSES

(75) Inventors: Hans Hörth, Hamburg (DE); Matthias Jürgens, Hamburg (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 119 days.

(21) Appl. No.: 10/388,253

(22) Filed: Mar. 13, 2003

(65) Prior Publication Data

US 2003/0176834 A1 Sep. 18, 2003

(30) Foreign Application Priority Data

Mar. 15, 2002 (EP) .............................................. 02005985

(51) Int. Cl.$^7$ .............................................. A61M 37/00
(52) U.S. Cl. .......................................... 604/85; 604/89
(58) Field of Search .............................. 604/81–93.01, 604/124, 181–182, 184, 187, 188, 191, 192, 200, 201–205, 208, 218, 221–222, 230, 231–237, 415–416; 366/602; 433/80–81, 88, 89–90; 222/630, 631, 55–58, 137, 386

(56) References Cited

U.S. PATENT DOCUMENTS 4,193,698 A   3/1980   Gartner 5,395,325 A   3/1995   Moreno et al.

FOREIGN PATENT DOCUMENTS

WO   WO 00/10479        3/2000
WO   WO 01/62317 A1    8/2001

OTHER PUBLICATIONS

European search report dated Sep. 2, 2002.

Abstract of JP1127858222 dated Oct. 12, 1999, Abstract only.

Primary Examiner—Nicholas D. Lucchesi
Assistant Examiner—Michael M Thompson
(74) Attorney, Agent, or Firm—Alix, Yale & Ristas, LLP

(57) ABSTRACT

The multi-component mixing capsule with dispensing device has a container part in which a component can be accommodated. A further component is arranged in a piston which is sealed at one end by a foil disk and a holed disk. At the other end, the piston is sealed by a ram which, in a first operating step, forces the liquid component from the piston into the mixing space of the container part and, in a second operating step, also forces the piston downward so that the mixed compound can emerge from the dispensing device.

20 Claims, 4 Drawing Sheets

MULTI-COMPONENT MIXING CAPSULE, IN PARTICULAR FOR DENTAL PURPOSES

BACKGROUND OF THE INVENTION

The invention relates to a multi-component mixing capsule with a dispensing device for the mixed compound, in particular for dental purposes, with a container part forming a mixing chamber which has a dispensing opening, with a piston which is displaceable in the container part and which has a holed wall delimiting the mixing chamber at its end remote from the dispensing opening and, on the other side of the holed wall, has a receiving chamber for a liquid component, and with a ram which, by means of a tool, can be displaced in the receiving chamber for the purpose of emptying the liquid component into the mixing chamber, the piston being supported directly or indirectly on the tool in relation to the tool force pushing the ram forward, and with a part of the piston which, in the rest state, protrudes beyond the rear end of the container part remote from the dispensing opening, having a radial projection which forms a support surface.

With a known multi-component mixing capsule of this type (DE 39 20 537 A1), several components can be mixed together and then dispensed. The several components are at first separate. A powder material in particular is present in the mixing chamber, while a second component in the form of a liquid is enclosed in a foil container. A tool is used to push the ram into the piston, which initially does not change its position relative to the container part. The foil container is destroyed in the process, and the liquid is forced by the ram into the mixing chamber. The mixing capsule is then removed from the tool and fitted into a conventional vibratory mixing unit. After the components have been mixed together in this way, the mixing capsule is once again inserted into the tool, and the ram is pressed farther into the container part. In doing so, it entrains the piston whose radial flange yields. In this way, the mixed compound is forced out of the mixing chamber for the desired application.

The disadvantage of this previously known device is that only relatively small amounts of liquid can be used in relation to the volume of the mixing capsule. This is because the foil container cannot of course fill the entire space of the receiving chamber, and instead unused space remains around the foil container.

It is an object of the invention to make available a mixing capsule of the type mentioned at the outset in which, compared to mixing capsules of the same size in the prior art, a much greater amount of the liquid component can be accommodated.

SUMMARY OF THE INVENTION

The solution according to the invention lies in the fact that the holed wall of the piston is sealed off on its outside with a foil and with a holed disk which encloses the foil between itself and the holed wall.

The liquid component is thus no longer arranged in a foil container, and instead it can fill the entire receiving chamber of the piston. The piston is in this case sealed at one end by the ram, while at the other end, where it has a holed wall, it is sealed with a foil. This foil is enclosed between the holed wall and a holed disk, which is applied to the foil from the outside.

It is of course known for corresponding pistons to be sealed off with a foil. However, if a foil is simply applied to the holed wall without any other measures (WO 00/10479), there is a great risk that the foil will tear off in an uncontrollable manner and fragments of the foil will be able to get into the mixed compound.

The sealing with the foil is expediently carried out after the receiving chamber of the piston is filled with the liquid component. Compared to a method in which the foil is first applied, then the liquid component is introduced and finally the ram is fitted, this has the advantage of permitting compression-free filling. If in fact the liquid is first introduced, there is a risk, upon insertion of the ram, that the foil will tear as a result of the overpressure which is generated. In addition, there may be air residues left in the receiving chamber which reduce the amount of the usable liquid volume. After the foil has been applied to the holed wall of the piston, the holed disk is applied to the foil. The hole in the holed disk then precisely defines a cross-sectional area in which the foil can burst. In this way, the destroyed area of the foil is kept very small, so that there is virtually no danger of parts of the foil getting into the mixed compound. In addition, the size of the hole in the holed disk can determine the pressure at which the foil tears. This can occur in particular as a function of parameters such as the viscosity of the liquid.

The foil is advantageously an aluminum foil. Aluminum has the advantage of acting as a good vapor barrier to the vapors from the liquid component. To allow the foil to be welded to the holed wall and the holed disk, which are advantageously made of plastic, the foil is plastic-coated. It would also be possible just to use plastic foils, making the arrangement simpler. In this case, the disadvantage of the lower vapor barrier effect can be partially obviated by using biaxially stretched plastic foils.

In the case of such plastic foils or plastic-coated aluminum foils, the foil can be welded to the holed wall and/or the holed disk, in particular welded by ultrasound, in order to avoid excessive heat which could cause the liquid component to evaporate or could have other disadvantageous effects. On the other hand, however, the foil can also be adhesively bonded to the holed wall and/or the holed disk.

Another possibility, in which welding or adhesive bonding may be dispensed with, is to mechanically secure the foil by means of the holed disk and to press the foil onto the holed wall with a labyrinth seal through the holed disk. A combination of these fastening methods is of course also possible. The possible ways of fastening and sealing the foil are to be chosen taking other considerations into account too. In the case of an aluminum foil coated with plastic, the aluminum is exposed at the cutting points, so that there is a danger of a chemical reaction occurring between the aluminum and acids. This area must therefore be sealed, welded or bonded so that the liquid component cannot come into contact with the aluminum. The connection could for example be made with a sealing wax or a quick-acting adhesive. To guarantee the action of the sealing ring, present on the ram, over a longer period of time, and to counteract possible fatigue of said sealing ring, the sealing ring or the whole ram can be covered with sealing wax.

As has been mentioned, the invention affords the considerable advantage that greater amounts of the liquid component can be arranged in the mixing capsule. Whereas comparable mixing capsules have hitherto been able to receive only 100 mg of liquid, an amount of 300 to 400 mg of liquid is possible in mixing capsules of the same size according to the invention.

BRIEF DESCRIPTION OF THE DRAWINGS

The invention is explained below on the basis of advantageous embodiments and with reference to the attached drawings, in which.

DETAILED DESCRIPTION OF THE PREFERRED EMBODIMENTS

Figure 1:
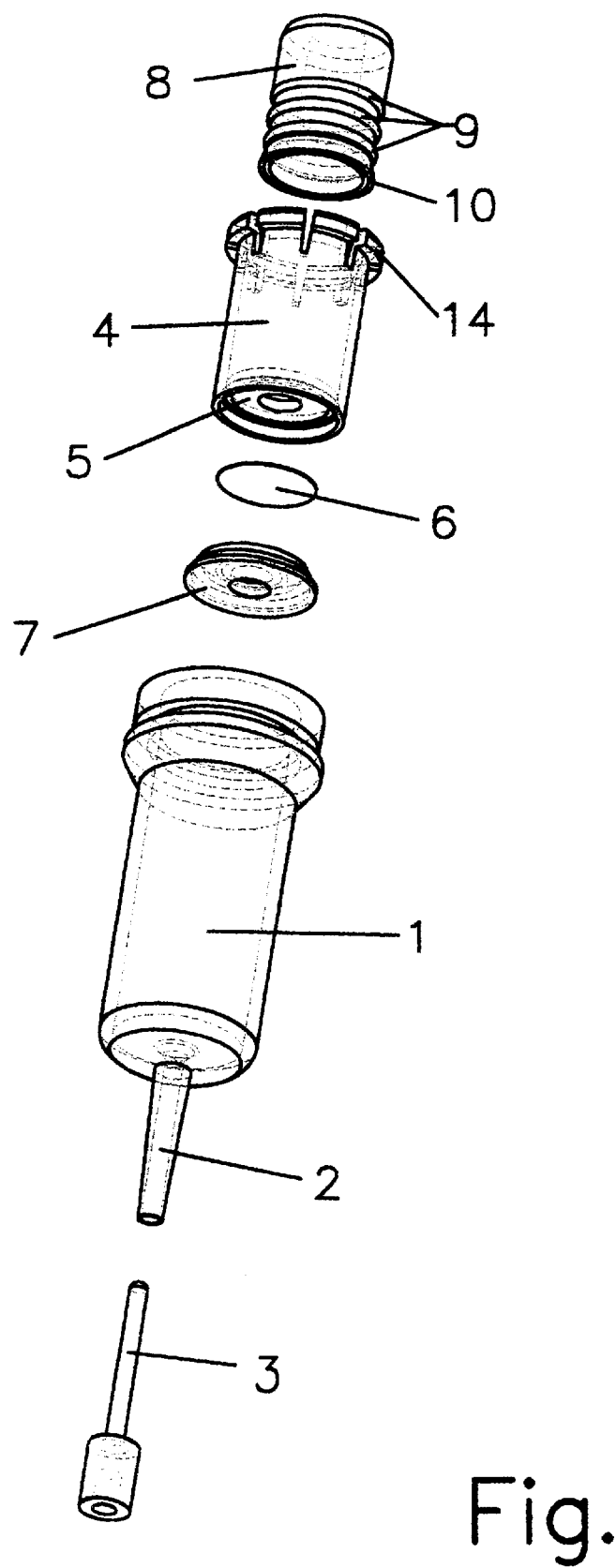
FIG. 1 shows a mixing capsule according to the invention in an exploded view.
Figure 2:
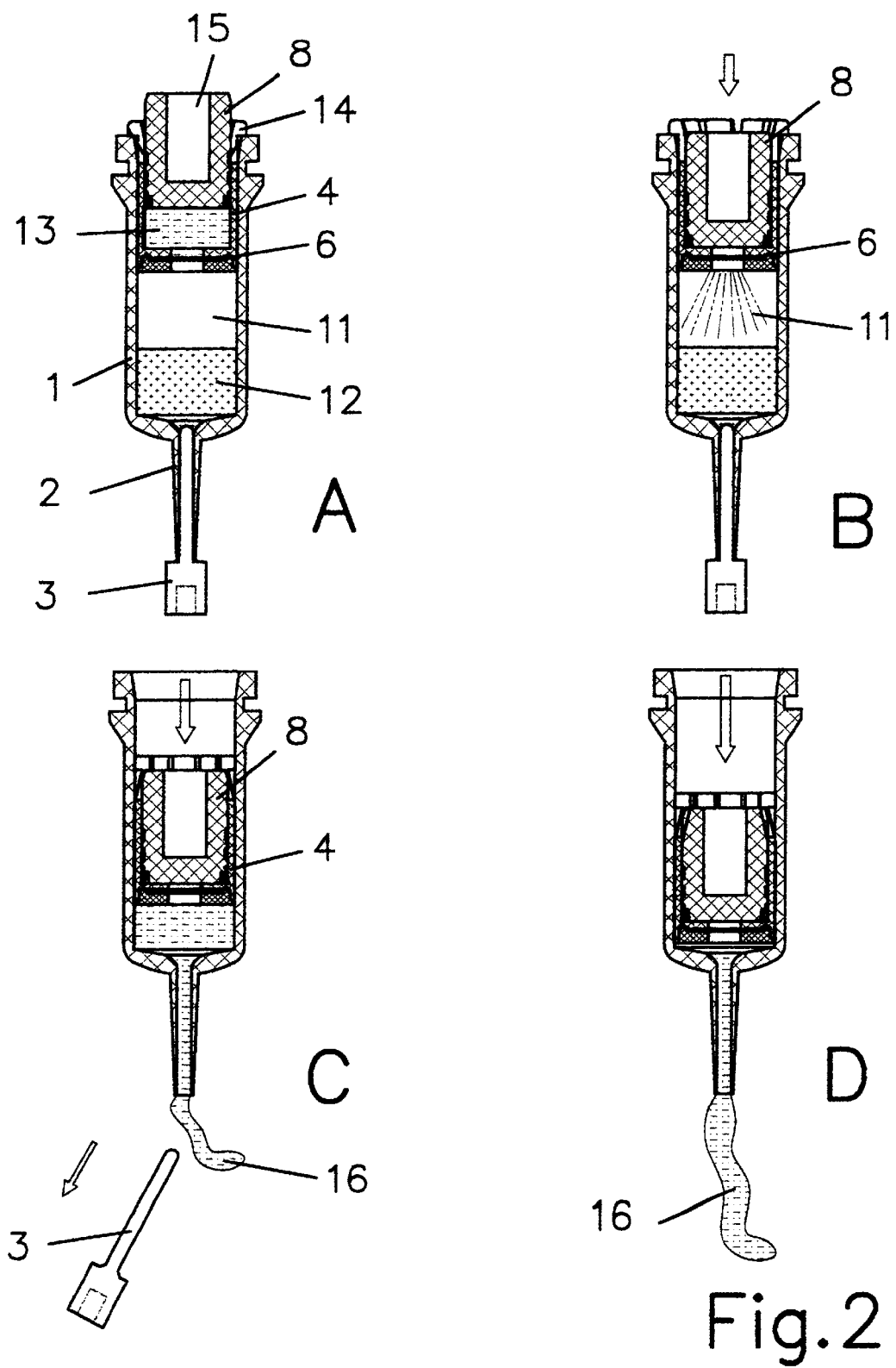
FIG. 2 shows the mixing capsule from FIG. 1 in cross section, in different stages of use.
Figure 3:
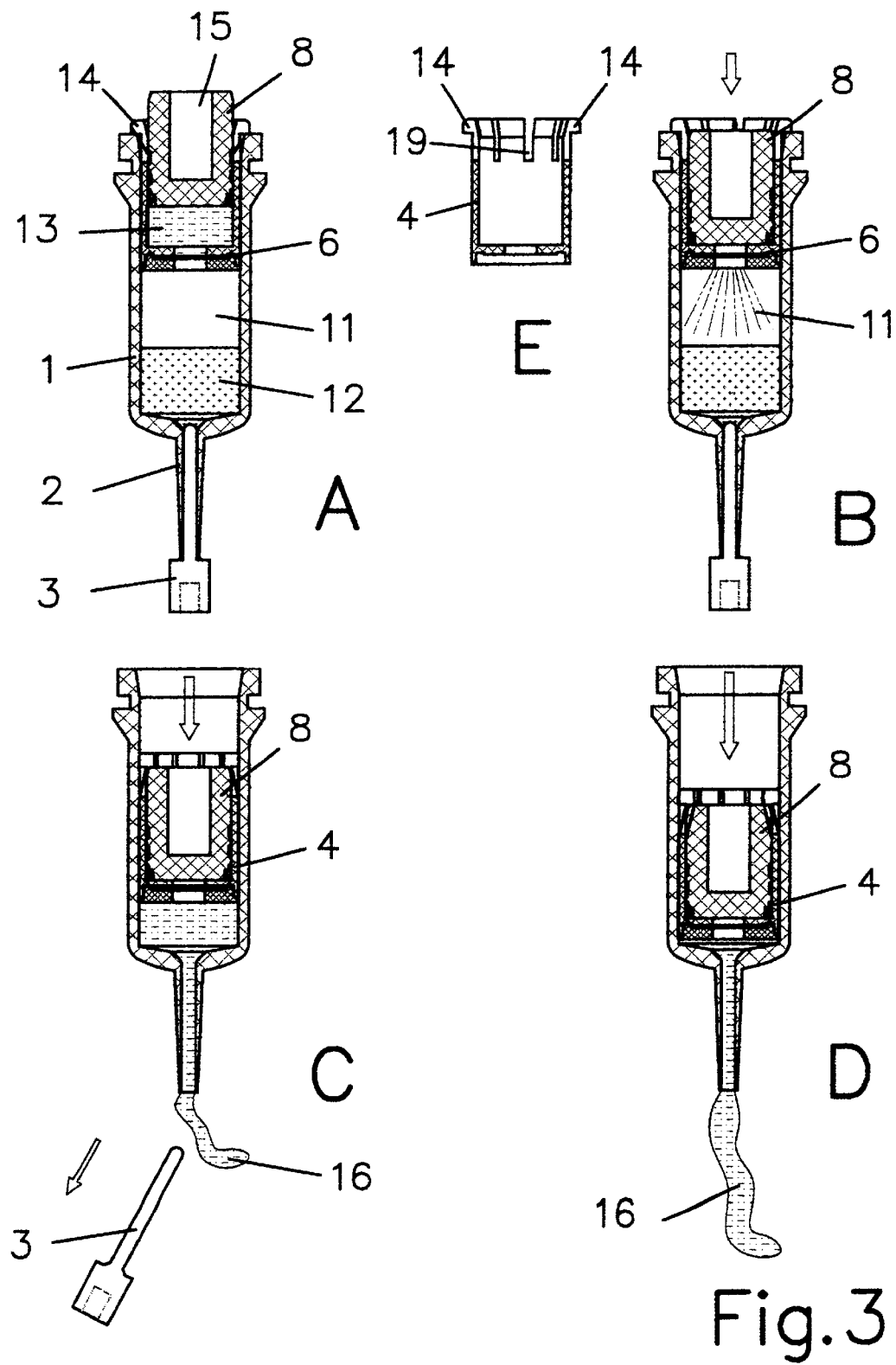
FIG. 3 shows another embodiment of the mixing capsule according to the invention, in different stages of use.

As is shown in FIGS. 1 to 3, the multi-component mixing capsule has a container 1 with an outflow channel 2 for the mixed compound, which outflow channel 2 can be closed by a needle 3. A piston 4 can be fitted into the container part 1, which piston 4 is open at the top and has a holed wall 5 at the bottom. The hole in the holed wall 5 can be closed by a foil disk 6, in particular of plastic-coated aluminum, and a holed disk 7 can then be applied to the holed disk 6 in o;:der to effectively support the foil mechanically at the edge and to permit controlled tearing open only within the hole of the holed disk 7. A ram 8 can be inserted into the upper, open end of the piston 4, which ram 8 has guide rings 9 and a sealing ring 10.

To fill the mixing capsule, the ram 8 is first inserted into the piston 4. With the holed wall 5 facing upward, the liquid component is then introduced into the receiving chamber of the piston 4. The foil disk 6 is then applied to the holed wall 5 and is secured mechanically with the aid of the holed disk 7. The foil 6 can be fastened both to the holed wall 5 and to the holed disk 7 by adhesive bonding, welding (in particular ultrasonic welding), sealing or the like. The holed disk 7 can additionally be mechanically secured by a screw connection, a snap-fit catch or the like. Then, after the other component has been introduced into the mixing chamber of the container part 1, the piston 4 is inserted into the container. The configuration represented at A in FIG. 2 is then obtained, in which a component 12, in particular a powder 12, is located in the mixing chamber 11, while the liquid component is arranged in the receiving chamber 13 of the piston 4. The plunger 4 is at this stage supported on the container part 1 with the aid of an annular projection 14. To use it, the mixing capsule is fitted into a tool (not shown) which presses the stamp 8, provided with a bore 15, into the piston 4. The piston 4 is at this stage secured in place by its annular projection 14, and only the ram 8 is pressed downward. As is shown at B in FIG. 2, the foil 6 now tears, and the liquid can penetrate into the mixing chamber 11. Once the state shown at B in FIG. 2 has been reached, the mixing capsule is removed from the tool and placed in a vibratory mixer. After the mixing has been carried out, the mixing capsule is once again fitted into the tool, and the ram 8 is pressed farther down by the tool, after the closure needle 3 has been removed. The annular projection 14, which is made of a suitably soft material, yields at this stage, so that the piston 4 is also pressed downward, with the result that the mixed compound 16 can emerge from the channel 2. This state is shown at C in FIG. 2, while D shows the situation when the mixed compound 16 has been pressed fully from the mixing capsule.

The embodiment in FIG. 3 corresponds substantially to that in FIG. 2. However, a difference is that there is not one projection 14 provided on the piston 4, but instead a plurality of projections 14, these being arranged on tongue-like ends 19 which are able to yield when the piston 4 is pressed into the container part 1. This ram is shown at E in FIG. 3. The views in Figures A, B, C and D in FIG. 3 otherwise correspond to the views in FIG. 2.

Figure 4:
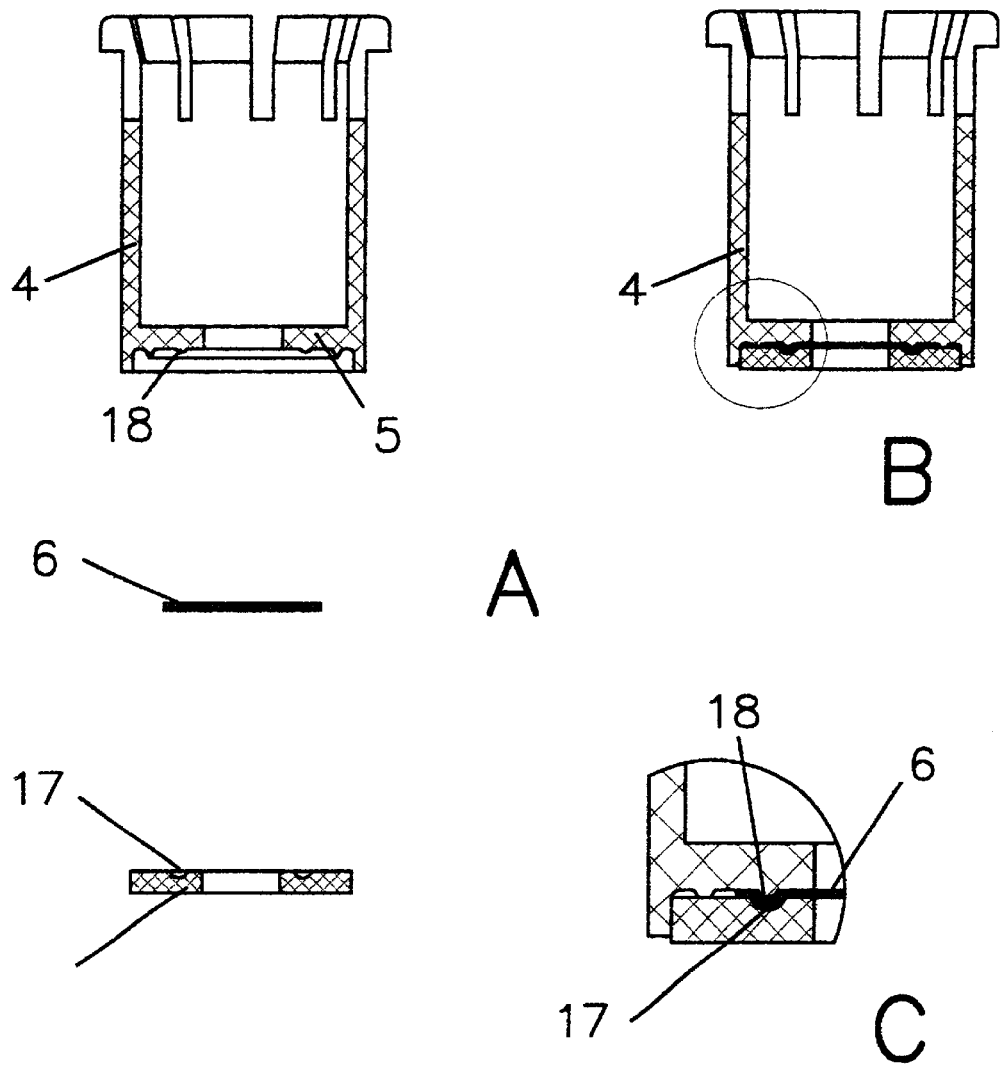
FIG. 4 shows an advantageous way of fastening the foil to the holed wall of the piston.

As has been stated, the foil disk 6 can be fastened to the holed wall 5 and/or the holed disk 7 by adhesive bonding, welding, sealing and the like, in order thereby to reliably seal off the receiving chamber 13 for the liquid component. Instead of this, or in addition, a labyrinth seal can be provided, as is shown in FIG. 4. At A in FIG. 4, the piston 4, the foil disk 6 and the holed disk 7 are shown prior to assembly. The holed disk 7 has circular recesses 17, and the holed wall 5 has corresponding complementary circular elevations 18. The foil 6 is clamped in between these in the finished state, as is shown at B. The part of View. B indicated by a circle is shown on an enlarged scale at C in FIG. 4.

What is claimed is:

1. A multi-component mixing capsule for dental purposes, with a dispensing device for the mixed compound, with a container part forming a mixing chamber which has a dispensing opening, with a piston which is displaceable in the container part and which has a holed wall delimiting the mixing chamber at its end remote from the dispensing opening and, on this side of the holed wall, has a receiving chamber for a liquid component, and with a ram which, by means of a tool, can be displaced in the receiving chamber for the purpose of emptying the liquid component into the mixing chamber, the piston being supported directly or indirectly on the tool in relation to the tool force pushing the ram forward, a part of the piston which, in the rest state, protrudes beyond the rear end of the container part remote from the dispensing opening, having a radial projection which forms a support surface, the holed wall of the piston being sealed off on its outside with a foil, wherein a holed disk is provided which encloses the foil between itself and the holed wall.

2. The multi-component mixing capsule as claimed in claim 1, wherein the foil is a plastic-coated aluminum foil.

3. The multi-component mixing capsule as claimed in claim 2, wherein the foil is welded to at least one of the holed wall and the holed disk.

4. The multi-component mixing capsule as claimed in claim 2, wherein the foil is adhesively bonded to at least one of the holed wall and the holed disk.

5. The multi-component mixing capsule as claimed in claim 2, wherein the foil bears via a labyrinth seal on at least one of the holed wall and the holed disk.

6. The multi-component mixing capsule as claimed in claim 2, wherein a plurality of radial projections are arranged on resilient tongues extending in the axial direction of the piston.

7. The multi-component mixing capsule as claimed in claim 1, wherein the foil is a biaxially stretched plastic foil.

8. The multi-component mixing capsule as claimed in claim 7, wherein the foil is welded to at least one of the holed wall and the holed disk.

9. The multi-component mixing capsule as claimed in claim 7, wherein the foil is adhesively bonded to at least one of the holed wall and the holed disk.

10. The multi-component mixing capsule as claimed in claim 7, wherein the foil bears via a labyrinth seal on at least one of the holed wall and the holed disk.

11. The multi-component mixing capsule as claimed in claim 7, wherein a plurality of radial projections are arranged on resilient tongues extending in the axial direction of the piston.

12. The multi-component mixing capsule as claimed in claim 1, wherein the foil is welded to at least one of the holed wall and the holed disk.

13. The multi-component mixing capsule as claimed in claim 12, wherein the foil bears via a labyrinth seal on at least one of the holed wall and the holed disk.

14. The multi-component mixing capsule as claimed in claim 1, wherein the foil is adhesively bonded to at least one of the holed wall and the holed disk.

15. The multi-component mixing capsule as claimed in claim 14, wherein the foil bears via a labyrinth seal on at least one of the holed wall and the holed disk.

16. The multi-component mixing capsule as claimed in claim 1, wherein a plurality of radial projections are arranged on resilient tongues extending in the axial direction of the piston.

17. The multi-component mixing capsule as claimed in claim 16, wherein seals on at least one of the piston and ram are covered with sealing wax.

18. The multi-component mixing capsule as claimed in claim 1, wherein the foil bears via a labyrinth seal on at least one of the holed wall and the holed disk.

19. The multi-component mixing capsule as claimed in claim 1, wherein seals of at least one of the piston and ram are covered with sealing wax.

20. The multi-component mixing capsule as claimed in claim 1, wherein the foil is welded to at least one of the hole wall and the holed disk by ultrasound.

* * * * *